United States Patent
Sato (10) Patent No.: US 7,413,527 B2
(45) Date of Patent: Aug. 19, 2008

(54) MUSCLE STRENGTH INCREASING TOOL

(75) Inventor: Yoshiaki Sato, Tokyo (JP)

(73) Assignee: Sato Sports Plaza Co., Ltd., Tokyo (JP)

( * ) Notice: Subject to any disclaimer, the term of this patent is extended or adjusted under 35 U.S.C. 154(b) by 0 days.

(21) Appl. No.: 10/568,593

(22) PCT Filed: Aug. 19, 2004

(86) PCT No.: PCT/JP2004/012236

§ 371 (c)(1),
(2), (4) Date: Feb. 17, 2006

(87) PCT Pub. No.: WO2005/018752

PCT Pub. Date: Mar. 3, 2005

(65) Prior Publication Data

US 2006/0281611 A1    Dec. 14, 2006

(30) Foreign Application Priority Data

Aug. 21, 2003    (JP) .............................. 2003-297979

(51) Int. Cl.
*A63B 21/00*    (2006.01)
*A61B 17/00*    (2006.01)
(52) U.S. Cl. .............................. 482/1; 606/202; 602/19
(58) Field of Classification Search ................. 600/479, 600/485, 490–497, 499; 606/202, 203; 602/5, 602/13, 19
See application file for complete search history.

(56) References Cited

U.S. PATENT DOCUMENTS 2,660,174 A * 11/1953 Saemann .................... 606/202

4,991,573 A * 2/1991 Miller ......................... 602/19

(Continued)

FOREIGN PATENT DOCUMENTS

JP        07-144027        6/1995

(Continued)

OTHER PUBLICATIONS

English language Abstract of KR2003-0025725A.

(Continued)

*Primary Examiner*—Glenn Richman
(74) *Attorney, Agent, or Firm*—Michael Bednarek; Paul, Hastings, Janofsky & Walker LLP (57) ABSTRACT

To provide a muscle strength increasing device for a pressure muscle training method that can easily be tied around a region to be compressed.

A muscle strength increasing device has a main belt 10 and a tie-down belt 20. A ring 11A and a loop-shaped belt 12A are fastened to the one end and the other end, respectively, of the main belt 10. The main belt 10 and the tie-down belt 20 are provided with two-dimensional fasteners 16, 21 for fastening. In order to tie the muscle strength increasing device around the region to be compressed, the region to be compressed is first passed through a loop of the main belt 10 that is formed by passing one end of the main belt 10 through the belt 12A. Then, the end of the tie-down belt 20 is passed through the ring 11A and turned right back. Thereafter, the tie-down belt 20 is pulled and the tie-down belt 20 is fastened to the main belt 10.

7 Claims, 6 Drawing Sheets

U.S. PATENT DOCUMENTS

| | | | | |
|---|---|---|---|---|
| 5,316,022 | A | * | 5/1994 | Schiek, Sr. ................ 128/876 |
| 5,413,582 | A | * | 5/1995 | Eaton ........................ 606/202 |
| 5,464,136 | A | * | 11/1995 | Eddy ......................... 224/666 |
| 6,149,618 | A | | 11/2000 | Sato |
| 6,237,602 | B1 | * | 5/2001 | Nickels et al. .............. 128/874 |
| 6,427,697 | B1 | * | 8/2002 | Pearcey ...................... 128/876 |
| 6,746,470 | B2 | * | 6/2004 | McEwen et al. ............ 606/202 |
| 7,070,572 | B2 | * | 7/2006 | Reinecke et al. ............... 602/5 |

FOREIGN PATENT DOCUMENTS

| | | |
|---|---|---|
| JP | 10-085361 | 4/1998 |
| JP | 10-085361 A | 4/1998 |
| JP | 10-085362 | 4/1998 |
| JP | WO00/10649 | 3/2000 |
| KR | 2003-0025725 A | 9/2001 |

OTHER PUBLICATIONS

English Language Abstracts of Japanese Patent Publication Nos. 07-144027;10-085361; 10-085362 and WO00/10649.
International Search Report.

* cited by examiner

MUSCLE STRENGTH INCREASING TOOL

TECHNICAL FIELD

The present invention relates to a muscle strength increasing device used for increasing muscle strength. More particularly, the present invention relates to a muscle strength increasing device suitable for a pressure muscle training method that allows healthy people as well as people having abnormalities of motor ability to increase their muscle strength in an effective manner.

BACKGROUND ART

The present inventor has conducted studies for some time in order to work out a muscle training method for easy, safe, and effective muscle development, and put together the accomplishments into a patent application having Japanese Patent Application No. 5-313949, which has been granted as Japanese Patent No. 2670421.

The muscle training method according to the subject patent, which involves the application of pressure, is a distinctive non-conventional one called a "Pressure Muscle Training Method". This muscle training method is based on the following theoretical concept.

Muscles are composed of slow-twitch muscle fibers and fast-twitch muscle fibers. Slow-twitch muscle fibers are limited in their potential for growth. Accordingly, it is necessary to recruit fast-twitch muscle fibers of the slow- and fast-twitch muscle fibers in order to develop muscles. Recruitment of fast-twitch muscle fibers causes lactic acid buildup in the muscles, which triggers secretion of growth hormone from the pituitary. The growth hormone has effects of, for example, promoting muscle growth and shedding body fat. This means that recruitment of fast-twitch muscle fibers results in development of fast-twitch muscle fibers and, in turn, the entire muscles.

Slow-twitch muscle fibers and fast-twitch muscle fibers are different from each other in terms of the following. Slow-twitch muscle fibers use oxygen for energy and are recruited for low-intensity activities. Fast-twitch muscle fibers provide for activities regardless of whether or not oxygen is present. They are recruited after the slow-twitch muscle fibers for highly intense, activities. Therefore, it is necessary to cause the earlier activated slow-twitch muscle fibers to be exhausted soon in order to recruit fast-twitch muscle fibers.

Conventional muscle strength increasing methods use heavy exercises with, for example, a barbell to cause the slow-twitch muscle fibers to be exhausted first, and then to recruit the fast-twitch muscle fibers. This recruitment of the fast-twitch muscle fibers requires a significant amount of exercises, is time-consuming, and tends to increase the burden on muscles and joints.

Conventional muscle training methods use exercises with, for example, a barbell to cause the slow-twitch muscle fibers to be exhausted first, and then to recruit the fast-twitch muscle fibers. This requires a significant amount of exercises, is time-consuming, and tends to increase the burden on muscles and joints.

On the other hand, when a predetermined range of muscles is pressurized to restrict the blood flow therethrough before muscle exercises, less oxygen is supplied to these muscles. The slow-twitch muscle fibers, which require oxygen for energy, are thus exhausted in a short period of time. Muscle exercises with blood-flow restriction by application of pressure will result in recruitment of the fast-twitch muscle fibers without needing a large amount of exercises.

In addition, restriction of the blood flow by application of pressure makes the lactic acid built up in the muscles less likely to be removed from the muscles. Thus, the muscle lactic acid level is more likely to rise and a much larger amount of growth hormone is secreted, as compared with the case where the blood flow is unrestricted.

Based on this theoretical concept, restriction of the muscle blood flow can provide significant development of the muscles.

The pressure muscle training method according to the aforementioned patent is premised on the theoretical concept of muscle strength increase by the restriction of blood flow. More specifically, a compression force for the blood flow restriction is applied to a range near the muscles that you want to develop and closer to the heart, i.e., a proximal region near those muscles. The compression force is controlled to put an appropriate stress attributed to blood flow decrease on the muscles, thereby causing muscle fatigue. Thus, effective muscle development is achieved.

This muscle training method features in muscle development without any exercises because it involves developing muscles by putting a stress attributed to blood flow decrease on the muscles. In other words, this muscle training method provides significant effects when applied to training for old people who do not exercises or rehabilitation for injuries, for example.

In addition, this muscle training method can compensate for a total amount of stress that is placed on the muscles by putting a stress attributed to blood flow decrease on the muscles. When combined with some exercises, the method advantageously reduces an exercise-related stress as compared with conventional methods. This advantage brings about some effects : the possibility of incurring damages to the joints or muscles can be reduced and the period of training can be reduced, as a result of decrease in amount of muscle exercises.

The present inventor invented a tight fitting band that restricts the blood flow using a compression force produced by a belt, which is disclosed in the aforementioned Japanese Patent Application No. 5-313949, as an implement that can put a stress on muscles by restricting the blood flow through the muscles, thereby achieving muscle development. The tight fitting band is for compressing a predetermined region to be compressed that is defined on at least one of the limbs of a wearer to restrict the blood flow through the limb while the tight fitting band is wrapped around the region to be compressed, to achieve muscle development.

However, such a tight fitting band also has a challenge to be solved.

That is, the aforementioned tight fitting band is wrapped twice around the region to be compressed during use. When a wearer tries to wrap the belt around the region to be compressed again after wrapping it once, the belt slips over the region to be compressed and turned around. To tie the belt around the region to be compressed is sometimes not so easy when being done without someone's help.

In particular, the pressure muscle training method is also suitable for those having some abnormalities of motor ability If the tight fitting band has a problem of not being able to be tied easily without someone's help around the region to be compressed, this may result in preventing widespread use of the pressure muscle training method.

The present invention is directed to provide a muscle strength increasing device that can be easily tied around the region to be compressed without someone's help.

SUMMARY OF THE INVENTION

The invention according to this application, which achieves the aforementioned object, is as follows.

The present invention is a muscle strength increasing device used for developing muscles by applying a predetermined compression pressure to a predetermined region to be compressed that is defined on at least one of the limbs of a wearer to restrict the blood flow through the limb. This muscle strength increasing device comprises a strip-shaped first band having a first hollow space formed therein at one end thereof; a strip-shaped second band the proximal end of which is connected to the proximal end of said first band, the second band having a second hollow space formed therein at a position near the end thereof through which the end of said first band can be passed; and a strip-shaped third band the proximal end of which is connected to the outer surface that is opposed to said region to be compressed when said region to be compressed is passed through a loop formed by said first and second bands by means of passing the end of said first band through said second hollow space of the proximal end of said first band, the end of the third band being formed so that it can pass through said first hollow space. In addition, at least said first band of said first band and said second band has an air-tight hollow tube along the length thereof in order to receive a gas from outside, and said first band and said third band are configured in such a manner that said third band can be attached to the outer surface (the surface of the first band wrapped around the region to be compressed that is away from the region to be compressed) of said first band after the end of said third band is passed through said first hollow space and turned right back.

This muscle strength increasing device can be tied around the region to be compressed by means of passing the end of the first band through the second hollow space formed in the second band to form a loop by the first band and the second band, and, in this state, passing the end of the third band into the first hollow space formed in the first band, then pulling the end of the third band to reduce the diameter of the aforementioned loop formed by the first band and the second band, and fastening the folded third band to the first band. In this case, the measure (length) of the loop formed by the first band and the second band is defined to be slightly larger than the circumferential length of the region to be compressed. As a result, the loop formed by the first band and the second band is not so easily turned around the region to be compressed when the region to be compressed is passed through the loop formed by the first band and the second band. In this state, the muscle strength increasing device can be tied around the region to be compressed only by means of pulling the third band with one hand. In other words, the muscle strength increasing device can be easily tied around the region to be compressed without someone's help because the aforementioned loop formed by the first band and the second band is not so easily turned around the region to be compressed.

Furthermore, this muscle strength increasing device has another advantage. For example, it is difficult to pass the leg with the region to be compressed through the aforementioned loop that is previously formed by the first band and the second band when it is desired to tie the muscle strength increasing device around the leg of a person who is confined to bed. This muscle strength increasing device is not provided as a loop from the beginning. Therefore, for example, the first band may be passed under the region to be compressed and then the loop is formed in the manner as described above, and then the third band may be pulled to tie it around the region to be compressed. In other words, this muscle strength increasing device can be easily tied around the region to be compressed even when the pressure muscle training is used for a person who has some troubles below the waist such as those who are confined with bed.

The muscle strength increasing device of the present invention is designed to compress the region to be compressed by means of introducing a gas into a tube to inflate the tube while it is tied around the region to be compressed. The tube may be provided across said first band and said second band.

The first band, the second band, and the third band are as described above. Details thereof are not specifically defined. For example, they may be made of a stretchable material or not. In addition, all of the first band, the second band, and the third band may be made of the same material or they may be made of different materials. The width and the length thereof may be determined appropriately depending on the limbs on which the region to be compressed is present (whether it is an arm or a leg) or according to the circumference of the limbs of a person who uses the pressure muscle training.

The first band, the second band, and the third band of the muscle strength increasing device may be formed separately. Alternatively, two of them, e.g., said first band and said second band may be formed as an integral part. In particular, the entire configuration of the muscle strength increasing device may be simplified when the first band and the second band are integrated with each other because they have the same function of forming the aforementioned loop.

In addition, said first band may be formed into a hollow bag. In this case, said tube may be provided within said first band.

Furthermore, when said first band and said second band are formed as an integral part, each of said first band and said second band may be formed into a hollow bag. Said tube may be provided within at least said first band of said first band and said second band. The tube may be provided across the inside of said first band and the inside of said second band.

The aforementioned first hollow space and the second hollow space may be formed by any one of appropriate means.

For example, in order to provide the first hollow space and the second hollow space, a ring, for example made of metal, may be attached to the end (or somewhere near the end) of the first band and the second band. In this case, the space inside the ring represents the first hollow space or the second hollow space.

By the way, the second hollow space directly faces against the region to be compressed. Therefore, there is a possibility that a person who uses the pressure muscle training has a pain when a hard material is used to form the second hollow space. With this respect, it is better not to use a hard material to form the second hollow space. For example, said second hollow space may be formed by providing a loop with a flexible, rope-like or belt-like material at the end of said second band. The flexibility of such a material should be of the extent that can prevent the person who uses the pressure muscle training from having a pain. Alternatively, the second hollow space may be formed by means of cutting a slit in the end of the second band. In this case, the second band is selected so that it does not cause a pain to the person who uses the pressure muscle training when it contacts the skin of the person who uses the pressure muscle training. It should be noted that the second band is expected to be contact with the skin of the person who uses the pressure muscle training. Therefore, the aforementioned conditions are satisfied as usual.

Details of the tube are not specifically defined as long as it is as described above. For example, it may be made of a stretchable material or may be made of a non-stretchable material, as long as it has appropriate air-tightness.

The tube in the muscle strength increasing device of the present invention may be designed to automatically inflate in the direction facing to said region to be compressed when it is filled with a gas while said third band is fastened to the outer surface of said first band. The inflation of the tube against the region to be compressed results in appropriate compression to the region to be compressed.

BRIEF DESCRIPTION OF THE DRAWINGS

FIG. 2 is a cross-sectional view of a main belt included in the muscle strength increasing device shown in FIG. 1;

FIG. 3A is an enlarged view of one end of the main belt included in the muscle strength increasing device shown in FIG. 1, while

FIG. 4A is a view showing a clip included in the muscle strength increasing device shown in FIG. 1, while

FIG. 5A is a horizontal cross-sectional view of an outer fabric of a main belt according to a modified embodiment in which a wire-like piece is used in place of a limit piece of the muscle strength increasing device shown in FIG. 1, while

BEST MODE FOR CARRYING OUT THE INVENTION

Now, referring to the drawings, a preferred embodiment of the present invention is described.

Figure 1:
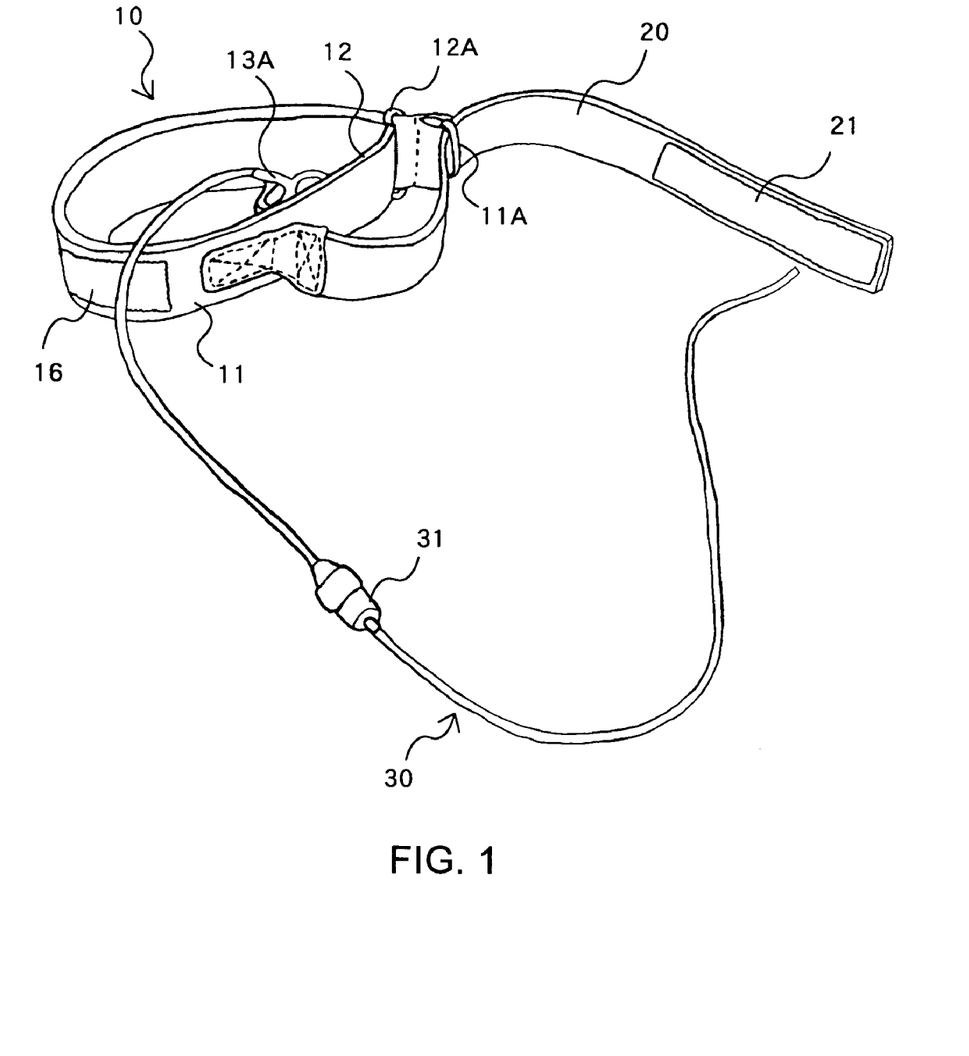
FIG. 1 is a perspective view of a muscle strength increasing device according to a preferred embodiment.
Figures 2, 3A:
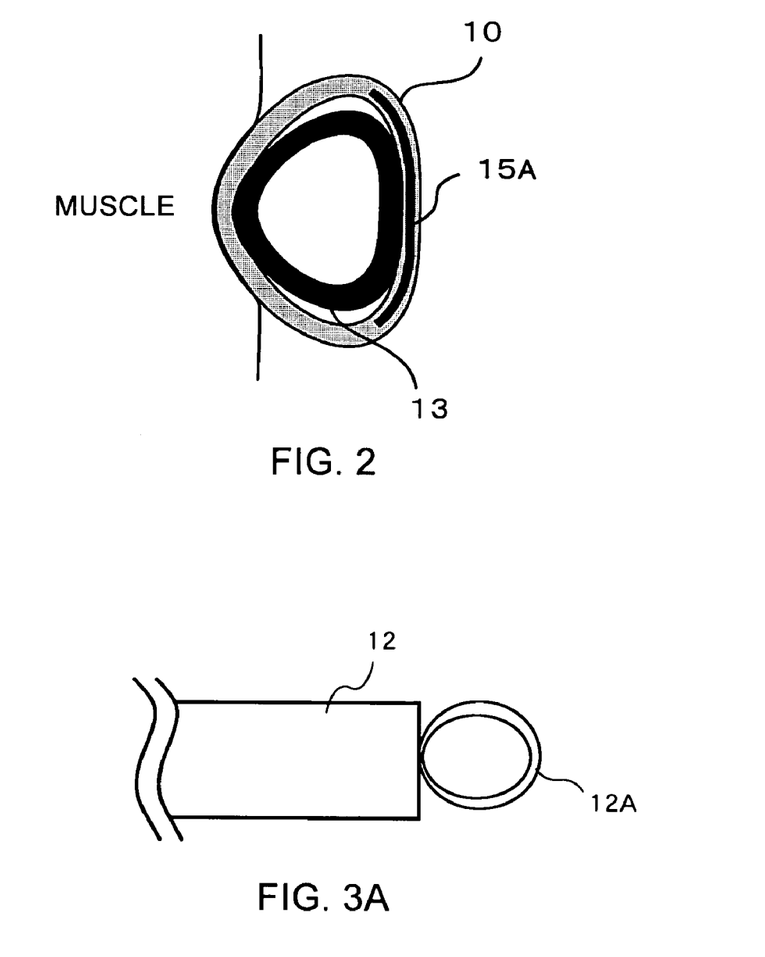

FIG. 1 is a perspective view showing a muscle strength increasing device according to an embodiment of the present invention. FIG. 2 is a cross-sectional view of a main belt in the muscle strength increasing device.

The muscle strength increasing device comprises a main belt 10 and a tie-down belt 20 attached thereto.

The main belt 10 includes a first band and a second band of the present invention. It corresponds to an integrated combination of the first band and the second band connected in series with each other. The longer portion 11 of the main belt 10 extending in one direction from where the tie-down belt 20 is attached corresponds to the first band of the present invention, and the shorter portion 12 extending in the opposite direction from where the tie-down belt 20 is attached corresponds to the second band of the present invention.

The main belt 10 is strip-shaped and, as shown in FIG. 2, is formed to be hollow in this embodiment. In this embodiment, two long strip-shaped pieces of fabric are bound by, for example, stitching or adhering them together along the lengthwise edges to form a hollow object having a space inside it. The main belt 10 has a predetermined stretchability. The aforementioned long strip-shaped pieces of fabric are made of a material that allows the main belt 10 to stretch. The length of the main belt 10 is equal to or slightly longer than the circumferential length of the region to be compressed that is compressed by the muscle strength increasing device. The length of the main belt 10 is determined appropriately according to whether the region to be compressed is an arm or a leg or according to the contour of a person who uses the pressure muscle training. On the other hand, the width of the main belt 10 is determined depending on the region to be compressed that is compressed by the muscle strength increasing device, i.e., according to whether the region to be compressed is an arm or a leg. In general, the width of the main belt 10 is wider for cases where the region to be compressed is a leg than for cases where the region to be compressed is an arm. In the former case, the width of the main belt 10 may be about 5 to 6 cm. In the latter case, the width of the main belt 10 may be about 3 to 4 cm.

The longer portion 11 of the main belt 10 extending in one direction from where the tie-down belt 20 is attached has a rectangular ring 11A at the end thereof. The ring 11A is made of a metal in this embodiment. The ring 11A is attached to the main belt 10 by means of slipping the aforementioned end of the main belt 10 through the ring 11A, turning the end right back and fastening it by, for example, stitching, to a point slightly away from that end of the main belt 10. The opening in the ring 11A corresponds to the first hollow space of the present invention through which the tie-down belt 20 can be slipped.

The shorter portion 12 of the main belt 10 extending in the opposite direction from where the tie-down belt 20 is attached has a narrow (about 1 cm in this embodiment) belt 12A as shown in FIG. 3A. This belt 12A is made of a flexible and stretchable material. The belt 12A is attached to the end of the main belt 10 as a loop with both ends thereof secured by, for example, stitching to the end of the shorter portion 12 of the main belt 10 extending in the opposite direction from where the tie-down belt 20 is attached. The space inside the loop of the belt 12A corresponds to the second hollow space of the present invention through which the end of the longer portion 11 of the main belt 10 extending in one direction from where the tie-down belt 20 is attached can be passed.

The cross section of the belt 12A is not limited to the illustrated one. It may be a circle. In such a case, the belt 12A is like a rope.

Figure 3B:
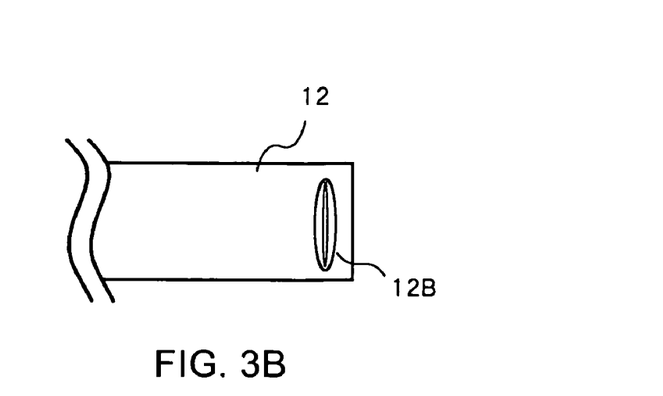
FIG. 3B is a view showing a modified version of the end of the main belt included in the muscle strength increasing device shown in FIG. 1.

Instead of using the belt 12A as described above, the end of the shorter portion 12 of the main belt 10 extending in the opposite direction from where the tie-down belt 20 is attached may have a cutout slit 12B as shown in FIG. 3B. In such a case, the slit 12B is formed so that the end of the longer portion 11 of the main belt 10 extending in one direction from where the tie-down belt 20 is attached can be passed therethrough. The slit 12B in this case corresponds to the second hollow space of the present invention as in the case of the space inside the loop of the belt 12A.

The hollow main belt 10 has a tube 13 therein as shown in FIG. 2. The tube 13 has air-tightness into which a gas can be introduced from outside. The tube 13 is generally equal in length to the main belt 10 and runs generally along the entire length of the main belt 10. The tube 13 may be made of, for example, a stretchable rubber that can withstand a pneumatic pressure of on the order of 300 mmHg. The tube 13 has a connection inlet 13A to which one end of a connecting pipe 30, which is a rubber tube, for use in introducing a gas can be connected. The connecting pipe 30 is connected to a pump (not shown) at the other end thereof and is used to introduce a gas into the tube 13. In other words, the tube 13 is supplied with a gas through the connecting pipe 30. The gas introduced into the tube 13 in this embodiment is air.

A connection piece 31 is provided on the connecting pipe 30 in this embodiment, but is not necessarily so. The connecting pipe 30 can be divided at the point of the connection piece 31. The connection piece 31 has a valve so that the gas cannot escape from the tube 13 even after the connecting pipe 30 is divided at the point of the connection piece 31. On the other hand, when the connecting pipe 30 is integrated at the point of the connection piece 31, the aforementioned valve automatically opens to allow the gas from, for example, the aforementioned pump to enter the tube 13.

Figure 4A:
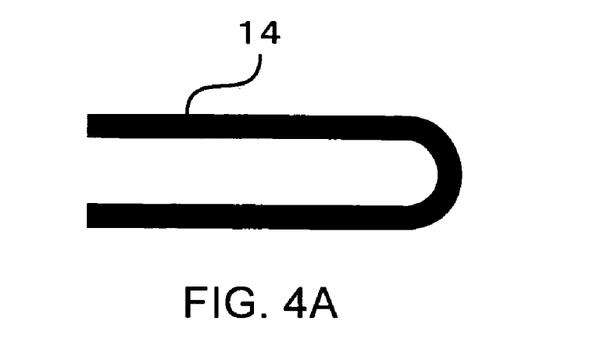
Figure 4B:
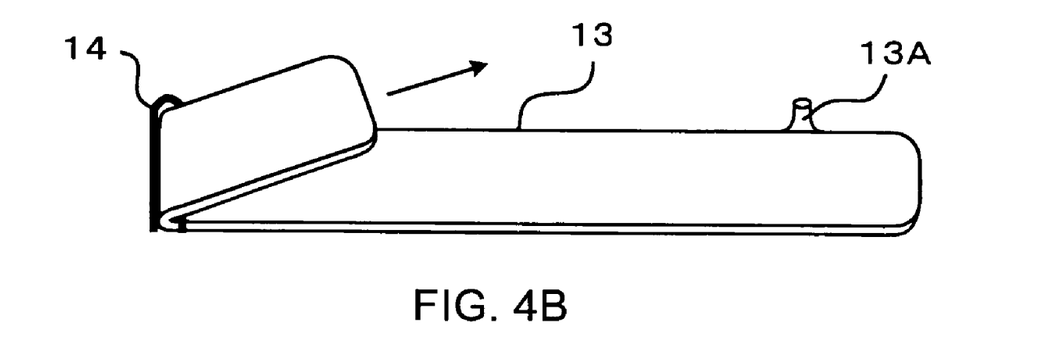
FIG. 4B is a view illustrating how the clip shown in FIG. 4A is to be attached.

The tube 13 in this embodiment is not fixed to the main belt 10. It may be removed through the opening formed in the main belt 10 to expose the connection inlet 13A. This is for the possible replacement of the tube 13 if the tube 13 is broken as well as for the use of a clip 14 shown in FIG. 4A. The clip 14 is for delimiting a range (length) of the tube 13 into which the air is allowed to enter. The clip 14 has a shape of a hairpin having two parallel straight segments and another segment connecting the one end of these two straight segments with each other. The length of the straight segment of the clip 14 is slightly longer than the width of the tube 13. The distance between the straight segments is slightly narrower to the thickness of the tube 13. When used, the clip 14 is attached to the tube 13 in the widthwise direction of the tube in such a manner that the clip pinches the tube 13 as shown in FIG. 4B. This can delimit the range into which the gas is introduced (the range inflated by the incoming air) of the tube 13 in the direction along the length of the tube. With the clip 14 used, the range of the tube 13 into which the gas is introduced is defined only along the portion that is other than the portion where the connection inlet 13A is not included (the bent portion at the left end of the tube 13 in the case of FIG. 4B).

The clip 14 provides following advantages. When the tube 13 is longer than the circumference of the range to be compressed of limbs, one end of the tube 13 is overlapped with the other end when the main belt 10 is fitted around the arm from the other end of the tube 13. Such overlapped portions of the tube 13 produce a gap between the tube 13 and the muscles, which may cause a trouble in that a compression pressure to be applied to the muscles by the main belt 10 becomes improper. Thus, the clip 14 is attached to the tube 13 at an arbitrary position along the length of it to restrict the length of the tube 13 that is filled with the air, thereby avoiding a problem as described above.

The outer section of the main belt 10 (the side opposite to the region to be compressed, as determined with the main belt 10 being tied around the region to be compressed) has a limit piece 15A therein along the outer contour of the tube 13, as shown in FIG. 2. The limit piece 15A is a plate-like object made of a polypropylene resin that is slightly narrower than the tube 13 and is generally equal in length to the tube 13.

The limit piece 15A is for limiting the direction towards which the tube 13 is allowed to inflate to the inward direction of the main belt 10 (to the side facing to the region to be compressed, as determined with the main belt 10 being tied around the region to be compressed). The muscle strength increasing device can appropriately compress the region to be compressed because the limit piece 15A forces to inflate the tube 13 only inwardly.

Figure 5A:
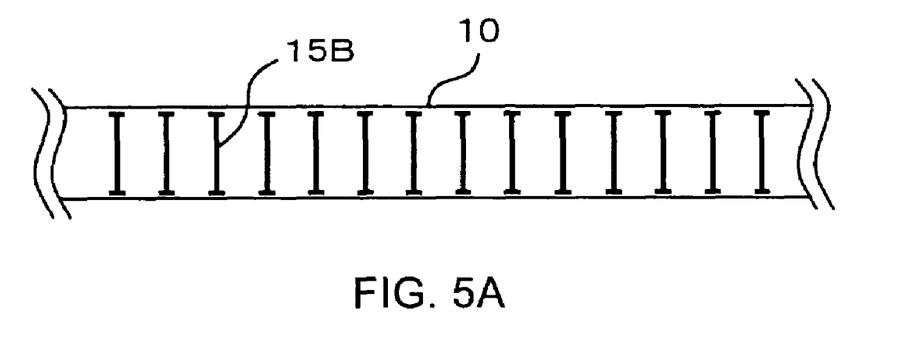
Figure 5B:
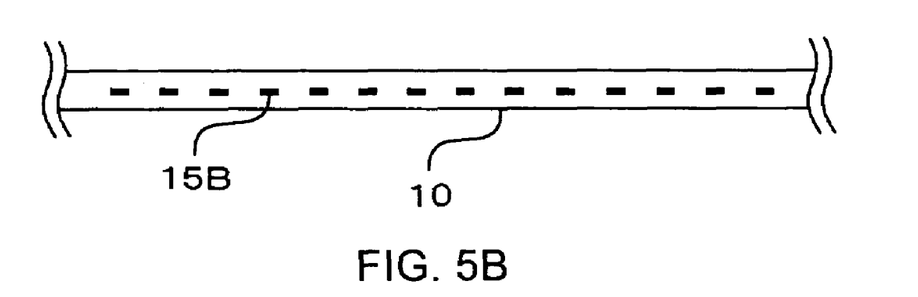
FIG. 5B is a vertical cross-sectional view of the outer fabric of the main belt.

It should be noted that a wire-like piece 15B as shown in FIG. 5 may be used in place of the limit piece 15A of the main belt 10.

In this case, wire-like pieces 15B having a constant hardness are provided within the outer fabric of the main belt 10 at a predetermined distance along the length of the main belt 10 in such a manner that they are generally in parallel to the widthwise direction of the main belt 10, as shown in FIGS. 5A and 5B. This may also provide appropriate compression of the region to be compressed by the muscle strength increasing device.

The aforementioned wire-like piece 15B may be made of a metal or a resin material. The distance between the adjacent wire-like pieces 15B may be, for example, 5 mm to 1 cm. The wire-like pieces 15B shown in FIG. 5 are described as being placed generally parallel to the widthwise direction of the main belt 10 but the wire-like pieces 15B may be any similar pieces that are provided in a direction not parallel to the lengthwise direction of the main belt 10.

The wire-like pieces 15B are illustrated as being embedded in the main belt 10, but they are not limited thereto. They may be provided inside the main belt 10. In this case, the wire-like pieces 15B may be fixed to the outside of the tube 13. For example, a plurality of wire-like pieces 15B may be placed on the inner surface of the main belt 10 that faces outside, generally in parallel to the widthwise direction of the main belt 10 and may be sealed with a stretchable tape having a surface with an adhesive applied thereto. Likewise, a plurality of wire-like pieces 15B may be adhered to the outer surface of the tube 13 with a tape having an adhesive applied thereto.

With the wire-like pieces 15B, flexible portions are provided between the adjacent wire-like pieces 15B, unlike the case where the limit piece 15A is used. Therefore, the main belt 10 can follow a complex up-and-down surface of the muscles when the main belt 10 is wrapped around the region to be compressed.

Figure 6:
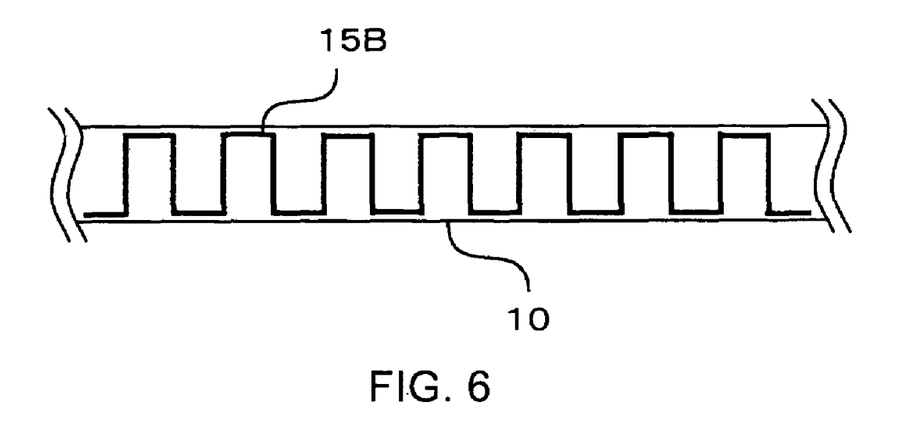
FIG. 6 is a cross-sectional view of a main belt according to yet another modified embodiment in which a wire-like piece is used in place of a limit piece in the muscle strength increasing device shown in FIG. 1.

Furthermore, the wire-like piece 15B that is used in the main belt 10 in place of the limit piece 15A may have a configuration as shown in FIG. 6. FIG. 6 is a cross-sectional view of an outer portion of the main belt 10. The wire-like piece 15B in this case is formed by bending a single wire-like piece. More specifically, the wire-like piece 15B in this case is formed by bending a single wire-like piece to put a series of angles in it and produce segments that are generally parallel to the widthwise direction of the main belt 10 at a predetermined distance. The requirement for the wire-like piece 15B is that it is bent to have a segment that is not parallel to the lengthwise direction of the main belt 10. For example, a wire-like piece may be bent into a zigzag pattern like a continuous series of "V"s. The wire-like piece 15B may be embedded in the outer portion of the main belt 10 or otherwise may be provided on the inside of the main belt 10 and the outside of the tube 13. The wire-like piece 15B formed by bending a single wire-like piece facilitates the attachment of the wire-like piece 15B to the main belt 10.

Figure 7:
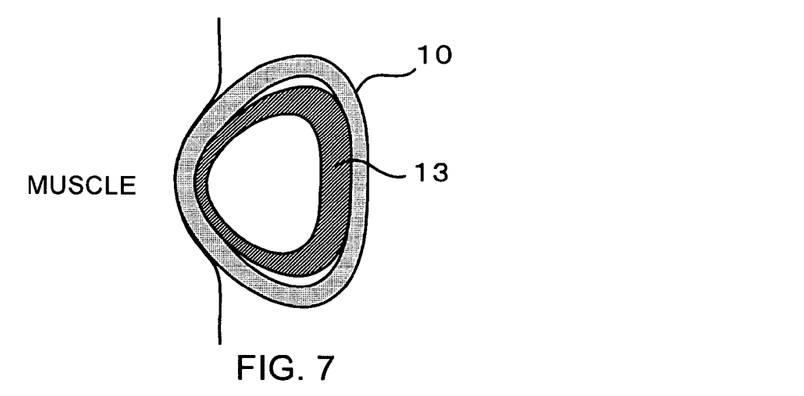
FIG. 7 is a cross-sectional view of a main belt according to another modified embodiment.
Figure 8:
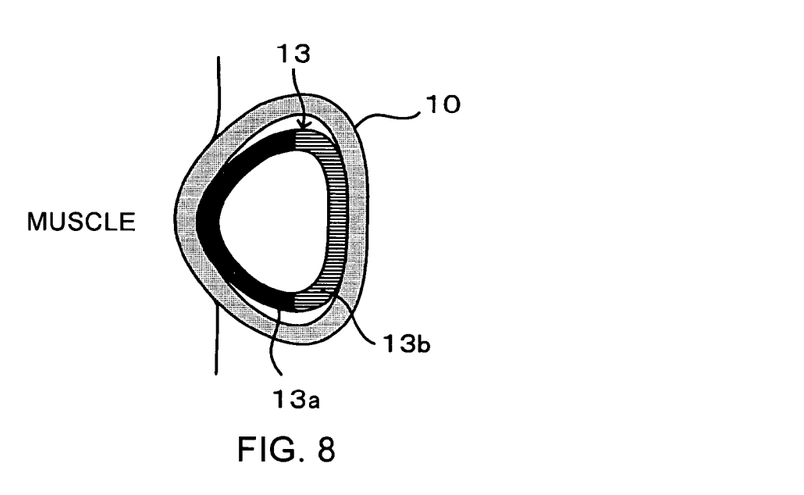
FIG. 8 is a cross-sectional view of a main belt according to another modified embodiment.
Figure 9:
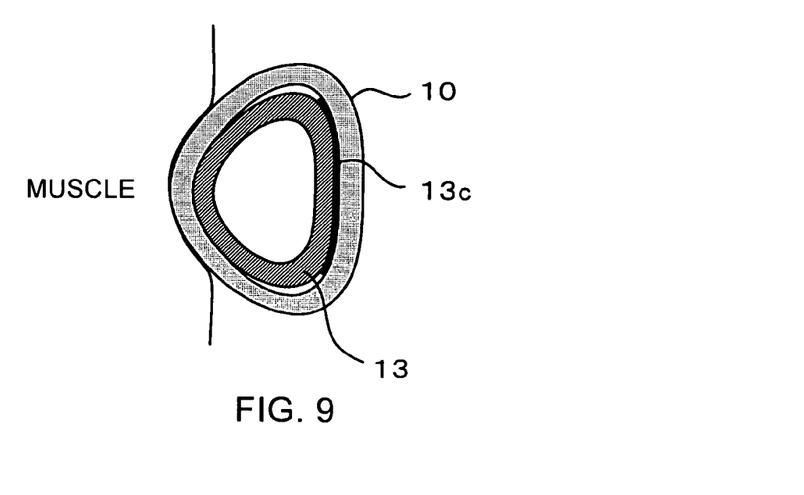
FIG. 9 is a cross-sectional view of a main belt according to another modified embodiment.

In addition, in place of using the limit piece 15A or the wire-like piece 15B, the tube 13 itself of the main belt 10 may have a configuration that allows the tube to inflate to the inward direction as shown in FIGS. 7, 8, and 9. The requirement for the tube 13 is that the tube is designed to have a higher stretching rate on the inner side than on the outer side, and the tube is also designed to inflate more in an inward direction as the tube 13 is filled with air with the main belt 10 being wrapped around a region to be compressed on the muscles.

The tube 13 shown in FIG. 7 represents an example of providing different stretching rates for the inner and outer portions of the tube 13 by changing the thickness of the tube 13. The tube 13 is made of a rubber and is thinner on the inner portion than the outer portion.

Furthermore, as shown in FIG. 8, the tube 13 in the main belt 10 may be made of a combination of different materials to achieve different stretching rates for the inner and outer portions of the tube 13. This tube 13 is a combination of two strip-shaped elastic bodies 13a and 13b having different stretching rates from each other, bonded along the sides thereof. The inner portion has a higher stretching rate than the outer portion. Accordingly, the tube 13 is inflated more in the inward direction as the tube 13 is filled with air with the main belt 10 being wrapped around the region to be compressed on the muscles.

In addition, as shown in FIG. 9, the tube 13 may be combined with a material having a lower stretching rate than the tube 13 to vary the stretching rates of the inner and outer portions of the tube 13. The tube 13 itself in this case has an equal stretching rate over the whole surface but a seam tape 13c having a lower stretching rate than the tube 13 is adhered to the outer surface thereof. This results in the tube 13 being inflated more, in the inward direction as the tube 13 is filled with air with the main belt 10 wrapped around the region to be compressed on the muscles.

On the outer surface of the main belt 10, a two-dimensional fastener 16 may be provided, for example. The two-dimensional fastener 16 is a Velcro tape in this embodiment. The two-dimensional fastener 16 is for attaching the tie-down belt 20 to the main belt 10 as will be described later. The fastener may be replaced by any other means as long as the above is possible.

The tie-down belt 20 corresponds to the third band of the present invention. The proximal end thereof is attached to the main belt 10. The tie-down belt 20 is attached to the main belt 10 by stitching it thereto in this embodiment.

The tie-down belt 20 has a two-dimensional fastener 21 on one surface thereof, as shown in FIG. 1. The two-dimensional fastener 21 is a Velcro tape in this embodiment. The two-dimensional fastener 21 is for the engagement with the aforementioned two-dimensional fastener 16 provided on the main belt 10. The fastener may be replaced by any other means as long as the above is possible.

The width of the tie-down belt 20 is slightly narrower than the width of the main belt 10 in this embodiment. The length of the tie-down belt 20 is determined so that the two-dimensional fastener 21 can be engaged with the two-dimensional fastener 16 on the main belt 10 after the tie-down belt 20 is slipped through the ring 11A and is turned right back with a predetermined tension applied to the tie-down belt 20.

Next, how the muscle strength increasing device is used is described with reference to FIGS. 10A to 10E.

Figure 10A:
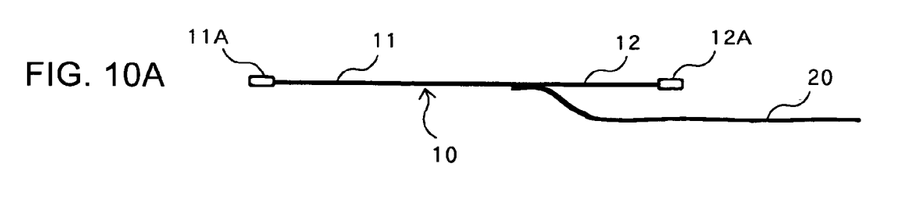
FIGS. 10A to 10E are views illustrating how the muscle strength increasing device shown in FIG. 1 is used.

First, prior to wrapping and tying the muscle strength increasing device around the region to be compressed, in this embodiment, the clip 14 is attached to the tube 13 at an appropriate position along the length of it. The circumferential length of the region to be compressed is measured first, and the clip 14 is attached to the tube 13 at the position to delimit the range into which the gas is introduced only to the length generally equal to the circumferential length of the region to be compressed. After the clip 14 is attached, the tube 13 is inserted back into the main belt 10. The muscle strength increasing device in this state is shown in FIG. 10A.

Figure 10B:
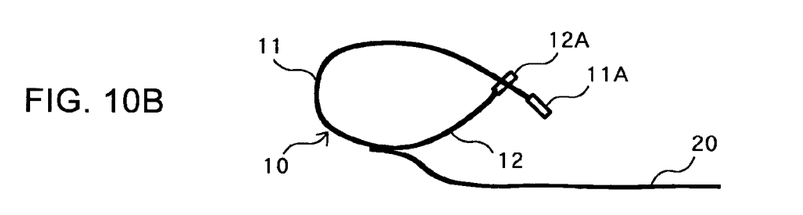

Next, the end of the longer portion 11 of the main belt 10 extending in one direction from where the tie-down belt 20 is attached is passed through the opening formed by the belt 12A. The muscle strength increasing device in this state is shown in FIG. 10B. The main belt 10 forms a loop now. The circumferential length of the loop is slightly longer than the circumferential length of the region to be compressed on which the muscle strength increasing device is rest.

Then, the end of the tie-down belt 20 is slipped through the space inside the ring 11A and the belt is turned right back. The muscle strength increasing device in this state is shown in FIG. 10C.

Figure 10C:
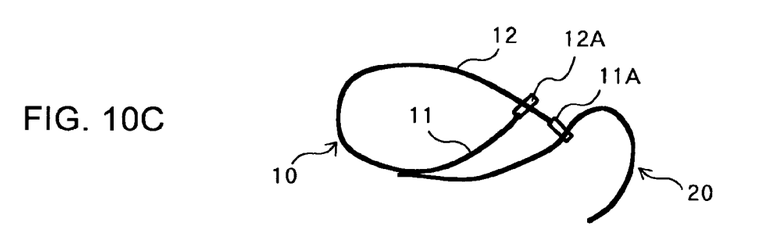

The arm or the leg of a person who uses the pressure muscle training is passed so that the region to be compressed falls inside the loop formed by the main belt 10 in the state shown in FIG. 10B or 10C.

Figure 10D:
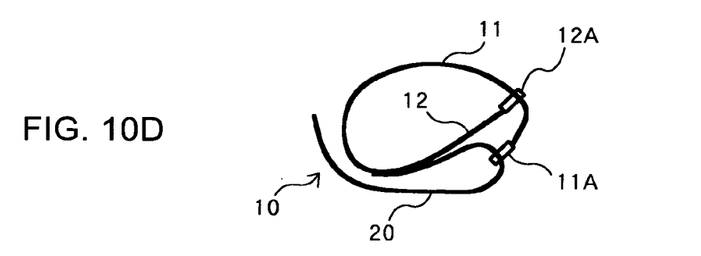

In this state, when the end of the tie-down belt 20 is pulled, the belt 12A moves to reduce the circumferential length of the loop formed by the main belt 10. The main belt 10 is thus placed around the region to be compressed without any gap. The muscle strength increasing device in this state is shown in FIG. 10D.

Figure 10E:
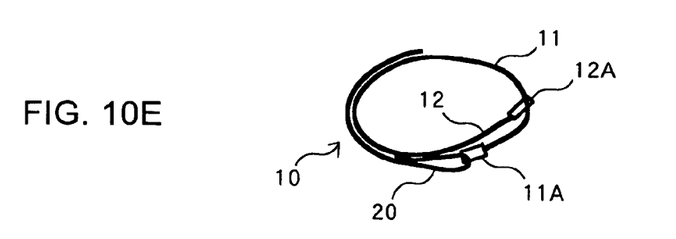

The tie-down belt 20 is pulled and the two-dimensional fastener 21 on the tie-down belt 20 is engaged with the two-dimensional fastener 16 on the main belt 10. This holds the muscle strength increasing device around the region to be compressed. The muscle strength increasing device in this state is shown in FIG. 10E.

After the arm or the leg of a person who uses the pressure muscle training is passed so that the region to be compressed falls inside the loop formed by the main belt 10, the muscle strength increasing device requires only to pull and tie the tie-down belt 20. This can be made with a single hand. In addition, the muscle strength increasing device does not turn around the region to be compressed. Therefore, the muscle strength increasing device is easy to be tied around the region to be compressed.

In this state, the gas is introduced into the tube 13 by using a pump (not shown). The tube 13 then inflates and compresses the region to be compressed in an appropriate manner.

A person who uses the pressure muscle training may do exercises or keep rest to achieve the pressure muscle training.

It should be noted that when a person who cannot tie by himself or herself the muscle strength increasing device around the region to be compressed due to, for example, being confined to bed uses the muscle strength increasing device, the main belt 10 of the muscle strength increasing device in the state shown in FIG. 10A is directly wrapped around the region to be compressed and then the aforementioned procedures follow. This allows to tie the muscle strength increasing device around the region to be compressed.

The invention claimed is:

1. A muscle strength increasing device used for developing muscles by applying a predetermined compression pressure to a predetermined region to be compressed that is defined on at least one of the limbs of a wearer to restrict the blood flow through the limb, the muscle strength increasing device comprising:

a strip-shaped first band having a first hollow space formed therein at a distal end thereof;

a strip-shaped second band a proximal end of which is connected to a proximal end of said first band, the second band having a second hollow space formed therein at a position near a distal end thereof through which the distal end of said first band can be passed; and a strip-shaped third band a proximal end of which is connected to an outer surface of at least one of the proximal end of the first band and the proximal end of the second band, the outer surface being opposed to said region to be compressed when said region to be compressed is passed through a loop formed by said first and second bands by means of passing the distal end of said first band through said second hollow space of the distal end of said second band, a distal end of the third band being formed so that it can pass through said first hollow space, said first band and said second band having an air-tight hollow tube along the length thereof in order to receive a gas from outside, said first band and said third band being configured in such a manner that said third band can be attached to the outer surface of said first band after the distal end of said third band is passed through said first hollow space and looped back so that the distal end of said third band extends in the same direction as from the distal end of the second band to the proximal end of the second band.

2. The muscle strength increasing device as claimed in claim 1, wherein said first band and said second band are formed as an integral part.

3. The muscle strength increasing device as claimed in claim 1, wherein said first band is formed into a hollow bag and said tube is provided within said first band.

4. The muscle strength increasing device as claimed in claim 1, wherein each of said first band and said second band is formed into a hollow bag and said tube is provided within said first band and said second band.

5. The muscle strength increasing device as claimed in claim 1, wherein said second hollow space is formed by providing a loop with a flexible, rope-like or belt-like material at the end of said second band.

6. The muscle strength increasing device as claimed in claim 1, wherein said second hollow space is formed by opening a space in said second band at the end thereof.

7. The muscle strength increasing device as claimed in claim 1, wherein said tube is designed to automatically inflate in the direction facing to said region to be compressed when it is filled with a gas while said third band is fastened to the outer surface of said first band.

* * * * *